United States Patent [19]
Schifano

[11] Patent Number: 5,015,243
[45] Date of Patent: May 14, 1991

[54] MEANS FOR REMOVING SMOKE FROM A OPERATIVE SITE

[76] Inventor: Michael Schifano, 2364 Mohawk, Glenview, Ill. 60025

[21] Appl. No.: 373,566

[22] Filed: Jun. 30, 1989

[51] Int. Cl.$^5$ .............................................. A61M 1/00
[52] U.S. Cl. ..................... 604/315; 604/317
[58] Field of Search ............... 604/313, 314, 315, 316; 55/385.8, 363, 529; 606/166, 40; 128/207.14

[56] References Cited

U.S. PATENT DOCUMENTS

| | | | |
|---|---|---|---|
| 452,131 | 5/1891 | Haughawout | 604/313 X |
| 2,338,339 | 1/1944 | La Mere et al. | 604/315 X |
| 3,074,407 | 1/1963 | Moon et al. | 606/166 |
| 3,958,965 | 5/1976 | Raczkowski | 55/385.8 |
| 3,973,936 | 8/1976 | Howard et al. | 55/363 |
| 4,082,092 | 4/1978 | Foster | 604/313 X |
| 4,619,259 | 10/1986 | Graybill et al. | 606/166 |
| 4,632,108 | 12/1986 | Geil | 128/207.14 |
| 4,688,570 | 8/1987 | Kramer et al. | 606/166 |
| 4,796,623 | 1/1989 | Krasner et al. | 606/166 |
| 4,826,513 | 5/1989 | Stackhouse et al. | 55/316 |
| 4,834,110 | 5/1989 | Richard | 604/176 X |
| 4,850,352 | 7/1989 | Johnson | 606/40 |
| 4,921,492 | 5/1990 | Schultz et al. | 604/315 |

Primary Examiner—Robert A. Hafer
Assistant Examiner—Kerry Owens
Attorney, Agent, or Firm—Hill, Van Santen, Steadman & Simpson

[57] ABSTRACT

A smoke evacuator is provided that includes a head member that substantially surrounds an operative site to draw air and smoke from around a perimeter of the site as the smoke is produced. The head can be secured about the site during the procedure.

19 Claims, 1 Drawing Sheet

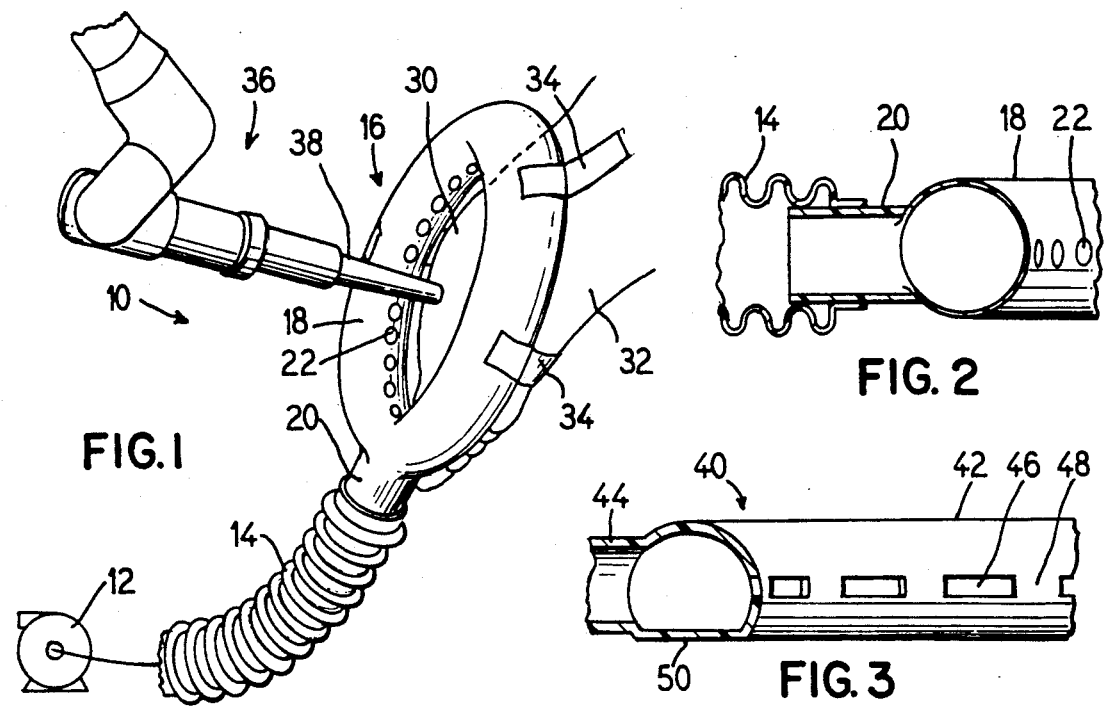
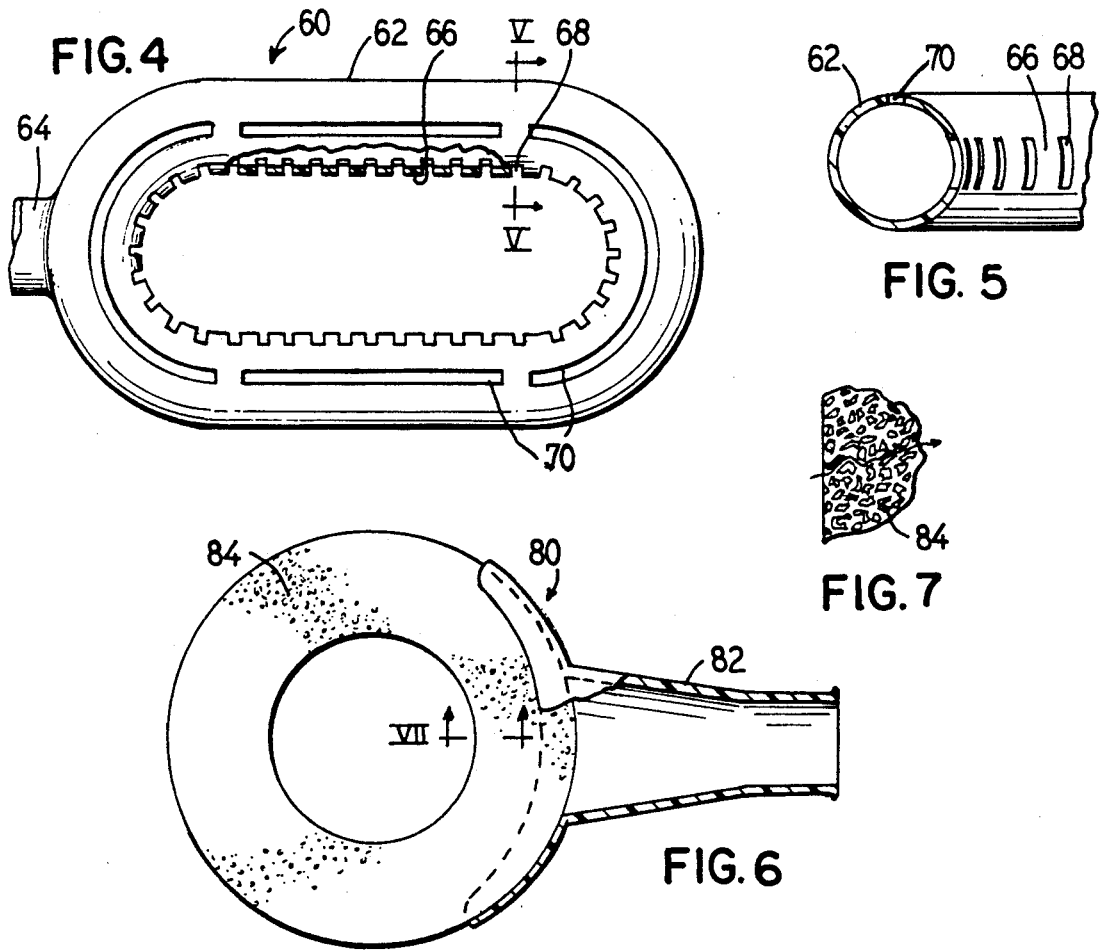

MEANS FOR REMOVING SMOKE FROM A OPERATIVE SITE

BACKGROUND OF THE INVENTION

The present invention generally relates to surgical instrumentation and procedures. More particularly, the invention relates to smoke evacuators for use in surgery.

In a variety of surgical and dermatological procedures, diseased or other tissue is destroyed as part of the operative procedure. In many cases, the tissue is destroyed by applying heat via a hot needle or laser beam to the tissue causing the tissue to be burned away. For example, warts and tumors can be removed in this manner. This procedure typically results in smoke being produced at the operative site as the tissue is destroyed.

For example, smoke plumes are generated during the dermatological procedure for ablation of verrucae. During the procedure, a laser beam is directed to the patient's skin, and as the tissue is destroyed, a plume rises from the destroyed tissue.

The health risks from inhaling the smoke generated during an operative procedure are not known. However, the smoke particulates are small enough in size to potentially cause lung and eye irritation. The long term effects of such irritation are also unknown. But, it is known that the smoke particulates may include viable viral contaminants as well as destroyed tissue.

There have been some attempts at providing smoke evacuation equipment. However, most of the efforts in this area have concentrated on filtering systems for filtering the smoke once it has been captured, rather than devices for capturing the plumes.

In a current practice, a nurse or assistant holds a suction tube adjacent an operative site to suck in the plume. During the procedure, the nurse or assistant attempts to follow the surgeon's hand with the suction tube to collect as much of the plume as possible.

It was reported in one study that "the amount of matter escaping into the air can be significantly increased if the suction apparatus is not closely approximated to the exposed tissue." J. Garden et al., *Papillomavirus in the vapor of carbon dioxide laser-treated verrucae*, JAMA 1988; 259:1199–1202.

From the results of this study, it can be inferred that, to provide for successful smoke evacuation adjacent an operative site, the suction apparatus must be as close as is feasible to the source of the plume. This close distance must be maintained throughout the operative procedure.

In laser surgery, the crucial responsibility of holding the suction wand has generally been placed fully on the free hand of the nurse or assistant who also has the simultaneous responsibility of operating the laser. This dual responsibility contributes to ineffective plume evacuation because the nurse's or assistant's attention is divided, and there is the possibility that the nurse or assistant can tire. Thus, in this method there is a great opportunity for the plume to escape.

SUMMARY OF THE INVENTION

The present invention provides a method and means for evacuating smoke plumes produced at an operative site. To this end, the invention includes a suction head that surrounds the operative site, the head having openings through which smoke produced at the operative site can be evacuated. The head can be secured about the operative site. An evacuator unit attached to the head creates the necessary vacuum to draw the smoke into the head.

In an embodiment, the invention includes a doughnut shaped tube member that is placed on the surface of an operative site. The tubular member surrounds the site so that the operative site falls within the center hole of the device. The tubular member includes a plurality of radial openings on an interior of the tubular member that face the operative site. A low pressure state is created with the tubular member so that any smoke produced at the operative site is drawn into the tubular member and evacuated from the site.

An advantage of the system of the present invention is that smoke produced during a surgical operation is immediately removed from an operative site.

Another advantage of the invention is that because smoke can be removed from the operative site, inhalation of such smoke is prevented or substantially reduced.

Yet another advantage of the invention is that the device is easily attachable to the surface of an operative site, thus eliminating the need for one to hold a suction tube in the proximity of the operative site.

These and other advantages will become apparent from the following description of the preferred embodiments thereof, taken in conjunction with the accompanying drawings.

BRIEF DESCRIPTION OF THE DRAWINGS

FIG. 1 is a perspective view of an embodiment device of the present invention positioned at an operative site;

FIG. 2 is a cross-sectional view of a neck portion of the device of FIG. 1 taken along lines II—II;

FIG. 3 is a cross-sectional view of an another embodiment of the device of the present invention;

FIG. 4 is a plan view of another embodiment of the device of the present invention;

FIG. 5 is a cross-sectional view of a portion of the device of FIG. 4 taken along lines V—V;

FIG. 6 is a plan view of another embodiment of the device of the present invention; and FIG. 7 is a cross-sectional view of a portion of the device of FIG. 6 taken along lines VII—VII.

DETAILED DESCRIPTION OF THE PRESENTLY PREFERRED EMBODIMENTS

A number of embodiments of the smoke evacuator devices of the present invention are illustrated in FIGS. 1–7. As discussed below, a common feature of each of these devices is the provision of effective static smoke suction about an operative site.

In FIGS. 1 and 2 there is illustrated a first embodiment 10 of the invention. In this embodiment, an evacuator pump 12 is operatively coupled to and in communication with a conduit 14. It can be appreciated that the pump 12 places the conduit 14 under a vacuum pressure.

The conduit 14 preferably is flexible, light weight, and suitable for use in an operating room. In the illustrated embodiment, the conduit 14 is a flexible corrugated tube made of plastic.

Operatively attached to the conduit 14 is an evacuator head 16. In the illustrated embodiment, the head 16 comprises a tubular ring member 18 having a radially projecting tubular neck member 20 that couples into an end of the conduit 14. The neck member 20 provides for fluid communication between the ring member 18 and the conduit 14.

As used herein, the terms "rings" and "ring-shape" refer to a member that surrounds a perimeter of a space. The term "ring," as used herein, encompasses both circular and oval shaped members.

As further illustrated in FIGS. 1 and 2, the ring member 18 includes a plurality of openings 22 positioned along an inner circumference of the ring member 18. The openings 22 are provided to allow air to be drawn from within the space surrounded by the ring member 18 into the ring member 18, through the conduit 14, and then out through the evacuator pump 10.

It can be appreciated that the shape of the openings 22 needed not be circular, as illustrated, but can be of any shape, including rectangular, hexagonal, etc. Further, the ring of openings 22 need not completely circumscribe as operative site. It is only important that air be drawn substantially in a surrounding fashion. Similarly, the ring member 18 need not completely surround the operative site either.

The evacuator head 16 is secured about an operative site 30, in FIG. 1, by a portion of a foot 32, by means of adhesive tpae strips 34. Of cource, other means can be used in place of the adhesive strips 32, the strips 32 merely comprise a very convenient means. For example, adhesive or double-sided adhesive strips could be located on that portion of the suction head that contacts a surface, generally, the patient's skin, surrounding the operative site.

In operation, the evacuator pump 12 serves to draw air from the operative site 30 through the opening 22. Any smoke produced by tissue burning devices, such as the laser 36, is similarly drawn through the openings 22.

It can be appreciated that, as the laser device wand 38 is moved about the operative site 30, smoke generated by the burning tissue is subject to a constant suction. As such, the evacuator head 16 serves to distribute vacuum pressure about the perimeter of the space of the operative site 30. Thus, there is no need to move a suction source alongside a tissue burning device so as to evacuate the smoke.

In FIG. 3, an embodiment of the evacuator head desi9n is illustrated. The evacuator head 40 includes a doughnut-shaped ring 42 and a neck 44. Slots 46 are formed along an inner circumference 48 of the ring 42. The slots 46 are elongated along the inner circumference 48.

Additionally, the doughnut-shaped ring 42 includes at least one side 50 that is flattened. By flattening the ring 42, better contact is afforded between a surface surrounding an operative site and the ring 42.

In FIGS. 4 and 5 there is illustrated another embodiment of the evacuator head. Therein, an evacuator head 60 is provided that includes a tubular oval 62 and a neck 64. The interior circumference of the oval 62 includes a plurality of slots 68 that ring the interior of the oval 62. As illustrated, the slots 68 are elongated perpendicular to the inner circumference 66.

The oval 62 also includes a plurality of slots 70 located along a topside thereof. The slots 70 are arranged to mimic the shape of the oval 62. The slots 70 provide a suction pressure along the topside of the oval to capture any smoke that may not have been captured through the slots 68.

In FIGS. 6 and 7, there is illustrated an embodiment of the evacuator head design. Therein, an evacuator head 80 is provided that includes a neck 82 that is attached to a ring 84. Preferably, the ring 84 is constructed from open celled foam, such as, for example, a sponge material. It can be appreciated that as air is drawn through the neck 82, air will be drawn through the ring 84 through the plurality of open cells. The plurality of open cells result in an evening out of the suction pressure causing a more even draw of air about the ring 84.

The disclosed embodiments provide a low profile evacuator head that does not impede or otherwise interfere with the operation. The low profile does not block a view to the operative site. Further, the low profile does not get in the way of moving hands, instruments, etc.

Further, because the disclosed evacuator heads are flexible, they can conform to the contour of whatever surface to which they are attached. Thus, the invention can be employed in a variety of situations, wherein the contour of the surface surrounding an operative sight is non-planar, just as easily as if the surface was planar.

Yet further, it can be appreciated that neither the evacuator head nor the tubing coupled thereto need have a circular or even substanitally circular cross-section. Mostly, the evacuator head, and tubing coupled thereto, need only provide a conduit surrounding an operative site for channeling smoke and air away from the operative site.

While preferred embodiments have been shown, modifications and changes may become apparent to those skilled in the art which shall fall within the spirit and scope of the invention. It is intended that such modifications and changes be covered by the attached claims.

I claim as my invention:

1. An apparatus for removing smoke from an operative site, comprising:
   (a) pump means for producing a source of vacuum pressure;
   (b) head means for distributing the vacuum pressure substantially around a perimeter of the operative site and including an open portion enscribed by said perimeter so as to be operative to permit a surgeon to perform a procedure within the perimeter; and
   (c) means for coupling the head pressure means to the pump means allowing the head means to remove smoke from about the perimeter of the operative site.

2. The apparatus of claim 1, including means for securing the head means about the operative site.

3. The apparatus of claim 1 wherein the head means comprises a hollow tubular ring with openings distributed about an inner circumference thereof.

4. The apparatus of claim 1 wherein the head means comprises a ring-shaped body of open celled foam.

5. The apparatus of claim 1 wherein the head means comprises an oval-shaped hollow member having openings distributed about an inner perimeter thereof.

6. The apparatus of claim 1 wherein the means for coupling comprises a hollow flexible tube.

7. The apparatus of claim 1 wherein the head means comprises a substantially ring-shaped member.

8. An apparatus for removing a laser generated smoke plume from an operative site, comprising:
   (a) a vacuum source;
   (b) a suction head member surrounding the operative site having means for drawing air from a space surrounded by the head member and including an open portion in registry with said space so as to be operative to permit a surgeon to conduct a procedure within said surrounded space; and
(c) means for coupling the vacuum source to the head member in fluid communication.

9. The apparatus of claim 8 wherein the head member coupling comprises a hollow flexible tube.

10. The apparatus of claim 8 wherein the head member comprises a ring-shaped hollow tube.

11. The apparatus of claim 8, including means for securing the suction head member about the operative site.

12. The apparatus of claim 8 wherein the head member operatively distributes a vacuum pressure about the space surrounded by the head member.

13. The apparatus of claim 8 wherein the head member comprises a body of open-celled foam.

14. In a method for removing smoke from an operative site of a patient, the steps of:
(a) generating vacuum pressure; and
(b) distributing the vacuum pressure with a head means substantially around a perimeter of the operative site and including an open portion enscribed by said perimeter so as to be operative to permit a surgeon to perform a procedure within the perimeter.

15. The method of claim 14 including the step of locating a suction head about the operative site.

16. The method of claim 14 including the steps of locating a suction head member about the operative site and distributing the vacuum pressure by drawing in air from the operative site through openings distributed about a perimeter of the suction head member.

17. The method of claim 14 including the step of ringing the operative site with a ring-shaped member that surrounds the operative site and that includes openings distributed about an interior perimeter thereof.

18. The method of claim 14 including the step of securing a suction head member about the operative site.

19. The method of claim 14 including the step of securing a suction head member about the operative site by means of adhesive.

* * * * *

UNITED STATES PATENT AND TRADEMARK OFFICE
CERTIFICATE OF CORRECTION

PATENT NO.   : 5,015,243
DATED        : May 14, 1991
INVENTOR(S)  : Michael Schifano It is certified that error appears in the above—identified patent and that said Letters Patent is hereby corrected as shown below:

Cover Page, in the Title, change "A" to --AN--.
Column 3, line 18, change "as" to --an--.
Column 3, line 24, change "tpae" to tape" and change "cource" to "course".
Column 3, line 44, change "desi9n" to --design--.

Column 4, line 23, change "substanitally" to --substantially--.

Signed and Sealed this

Twenty-seventh Day of October, 1992

Attest:

DOUGLAS B. COMER

*Attesting Officer*       Acting Commissioner of Patents and Trademarks